United States Patent
Hart et al.

(10) Patent No.: US 7,280,196 B2
(45) Date of Patent: Oct. 9, 2007

(54) SPECTROPHOTOMETER AND SUBASSEMBLIES THEREOF

(75) Inventors: Robert H. Hart, Cary, NC (US); Montie W. Roland, Cary, NC (US)

(73) Assignee: GretagMacbeth LLC, New Windsor, NY (US)

(*) Notice: Subject to any disclaimer, the term of this patent is extended or adjusted under 35 U.S.C. 154(b) by 399 days.

(21) Appl. No.: 10/784,595

(22) Filed: Feb. 23, 2004

(65) Prior Publication Data

US 2004/0233428 A1 Nov. 25, 2004

Related U.S. Application Data

(60) Provisional application No. 60/449,548, filed on Feb. 24, 2003.

(51) Int. Cl.
*G01J 1/04* (2006.01)
*G01J 3/42* (2006.01)

(52) U.S. Cl. ..................... 356/236; 356/319

(58) Field of Classification Search ............. 356/236, 356/318, 402, 326, 319; 250/228, 226
See application file for complete search history.

(56) References Cited

U.S. PATENT DOCUMENTS

| 5,369,481 | A | 11/1994 | Berg et al. |
| 6,424,413 | B1 | 7/2002 | Weber et al. |
| 6,583,879 | B1* | 6/2003 | Berg et al. ............ 356/402 |
| 2001/0013931 | A1 | 8/2001 | Sato |

OTHER PUBLICATIONS

Disclosure re: NationalHousewares.com website (acknowledged as prior art for purposes of this application).
GretagMacbeth literature, Color-Eye® 7000A Reference Spectrophotomer, 4 pages.

* cited by examiner

*Primary Examiner*—Layla G. Lauchman
(74) *Attorney, Agent, or Firm*—McCarter & English, LLP

(57) ABSTRACT

A spectrophotometric system includes a zoom lens assembly that is mounted for axial translation relative to an integrating sphere. The zoom lens assembly includes first and second focusing lens mounted to an axially movable lens carrier. The lens carrier is positioned intermediate first and second sets of mirrors for reflecting/directing SCE and SCI beams toward fiber ports. A reference beam is also emitted from the integrating sphere and transmitted to a processor, thereby resulting in simultaneous tri-beam measurements. The disclosed spectrophotometric systems may also include an aperture plate detection assembly and/or a sample holder assembly that incorporates a dampening gas spring. The aperture plate detection system includes a detection disk that may include a plurality of pre-positioned sensors that interact with an activating ridge formed on the aperture plate for identification thereof.

12 Claims, 8 Drawing Sheets

US 7,280,196 B2

SPECTROPHOTOMETER AND SUBASSEMBLIES THEREOF

CROSS-REFERENCE TO RELATED APPLICATIONS

The present application claims the benefit of a co-pending and commonly assigned provisional patent application entitled "Enhanced Spectrophotometer and Subassemblies Thereof," Ser. No. 60/449,548, which was filed on Feb. 24, 2003. The entire contents of the foregoing provisional patent application are hereby incorporated by reference herein.

BACKGROUND

1. Technical Field

The present disclosure relates to enhanced spectrophotometer systems and subassemblies/components associated therewith. More particularly, the present disclosure relates to spectrophotometer systems and subassemblies/components thereof that provide and/or facilitate: (i) simultaneous measurement of "specular included" and "specular excluded" reflectance properties of a sample through an innovative zoom lens assembly; (ii) transmission measurements of virtually unlimited areas of interest through an innovative zoom lens assembly; (iii) automated and reliable determinations of the type of aperture plate placed at the front of the spectrophotometric instrument through an innovative aperture plate detection assembly; and (iv) reliable and non-disruptive sample placement through an innovative sample holder assembly.

2. Background Art

The use of integrating spheres as an optical measurement geometry in reflectance colorimetry is a standard practice, and is described in the Commission Internationale De L'Eclairage (CIE) Publication Number 15.2 (Colorimetry), 1986, the disclosure of which is hereby incorporated by reference herein. An integrating sphere is a hollow metal sphere, generally several inches or more in diameter, that is coated with a highly reflecting diffuse material, e.g., barium sulfate or polytetrafluoroethylene. Thus, an integrating sphere generally defines an interior cavity (typically spherical) having a highly reflective, optically diffuse white surface.

The simplest integrating sphere designs contain two apertures, one which admits light and another which serves as a measurement port where the amount of light on the surface of the sphere can be measured. The integrating sphere generally collects all the light reflected from the surface of a sample placed against an opening into the sphere. At any point on the inner surface of the sphere, the illumination is essentially independent of the direction and location of the incident beam as well as the size of the beam; the inner surface is uniformly illuminated throughout, except at the point of direct illumination. By placing a specular port at an opposite angle (relative to the normal angle offset), the specular reflection can be either included or excluded from the measurement by placing material identical to the sphere's interior or a black trap, respectively, at the specular port. Integrating spheres are generally used in colorimetry for the precise determination of color for a sample under test.

It is a common practice in colorimetry to measure a sample with the specular component of reflection (mirror-like reflection from the surface) either included (SCI mode) or excluded (SCE mode). Other measurement-related parameters may include selection of the size of the measured sample surface, spectral content of the illumination, and angle of receiver beam with respect to the sample normal. Historically, instruments designed for colorimetry have measured the sample one configuration at a time (e.g., SCI or SCE mode with a single size of measured area), usually requiring a change of configuration or another instrument to select another mode combination. In such instruments, the integrating-sphere calorimeter is generally capable of measuring the sample with the specular component either included or excluded. Changing between SCI and SCE modes is usually achieved by the use of a movable segment of the integrating sphere which removes the specular component for SCE measurements or includes the specular component for SCI measurements. In such an instrument, the included/excluded option requires separate measurements with a time between to move the segment and mechanical means to do so.

Many instruments are capable of selecting the size of the area of the sample surface to be measured. Size selection is usually done with a "zoom" optical system or movable lens(es)/aperture(s). In such instruments, changing the size of the measurement area generally requires separate measurements with an inherent delay associated with moving the lens(es)/aperture(s). Mechanical structures for repositioning the lens have also been provided. Many instruments also use a second optical path as a reference measurement to normalize/compensate for changes in the illumination. Such common practice is generally referred to as "dual beam" optics.

Certain commercially available spectrophotometers in the color industry incorporate a method by which aperture plates corresponding to different aperture sizes are detected or selected so that the instrument can be properly configured to make the desired measurement with respect to the optical properties of the system in order to measure the correct area of interest. However, current methodologies for automatic aperture plate detection disadvantageously require a specific orientation of the aperture plate and typically use an optical sensor to determine the presence of a plate and the plate type. Commercially available methodologies for aperture plate detection are unacceptably limited and unreliable.

Bench top spectrophotometers in the color industry generally use a sample holder device to secure the sample under test to the instrument. Typical commercial systems are constructed using an "over-centered spring" design which allows the "sample arm" to be pulled away from the instrument (thus releasing the sample under test) and to maintain its open state once the "over-centered" position is reached. A major draw back to the foregoing "over-center" design is that, once the sample arm is moved from the "over-centered" position, it "mouse-traps" or springs back on the sample with great force. This force is frequently sufficient to damage the delicate coating of the illumination sphere in the area where the sample is typically placed, thereby imparting undesirable damage to the instrument and an attendant cost and interruption in use to the system user.

Colorimetry instruments with multiple measurement paths, e.g., measurement paths for simultaneously measuring sample SCI and SCE, are known. For example, U.S. Pat. No. 5,369,481 to Berg et al. discloses a portable spectrophotometer that includes a small-diameter optical sphere as well as optical detectors and signal processing and display circuitry which allow the instrument to be taken to an object to be measured and which provide a readout of color values at the portable instrument. The instrument is capable of providing specular-included and specular-excluded color readings simultaneously. The sphere is provided with a first aperture which receives spectrally-included light and which is positioned to absorb a spectral component of the diffused source light. A second aperture positioned at a corresponding angular position with respect to the object measures specular-excluded light, excluding the specular component absorbed by the first aperture. Light detected from the first aperture is analyzed at a plurality of wavelengths obtained by the use of interference filters, and the light obtained from the second aperture is analyzed at one of the plurality of wavelengths. By combining the specular-included and specular-excluded at one wavelength, a value for the specular component is derived. Since this value is a theoretical constant, it is used to derive a specular-excluded reading from each of the specular-included readings at the different wavelengths.

Commonly assigned U.S. Pat. No. 6,424,413 to Weber et al. describes a multi-channel integrating sphere and an integrating sphere-based reflectance colorimeter/spectrophotometer for the measurement of color and appearance The Weber '413 patent discloses devices that include multiple receivers capable of concurrently receiving optical radiation scattered/reflected from a diffusely illuminated sample surface, with the capability of multiple measurement modes (e.g., multiple specular component excluded (SCE), SCE and specular component included (SCI), multiple SCI), multiple areas-of-view for a given measurement mode, multiple viewing angles per measurement mode, and combinations thereof. In a disclosed embodiment, two SCI receivers and two SCE receivers are provided, each disposed at an equal viewing angle relative to the sample surface. For each viewing mode, two sample areas-of-view are provided. The SCE receivers are opposite each other, such that the specular component of each SCE receiver is excluded by the port of the other SCE receiver. The receivers provide the collected light reflected from the sample to a detector which preferably is provided by multiple spectrometers or a single spectrometer having multi-channel capability to preferably sense the light from each receiver in parallel. The entire contents of the Weber '413 patent are hereby incorporated herein by reference.

Despite efforts to date, a need remains for enhanced colorimetric/spectrophotometric systems and subassemblies/components thereof having certain desirable features and functionalities. In particular, a need remains for colorimetric/spectrophotometric systems and subassemblies/components thereof that provide enhanced zoom lens functionalities and/or capabilities, enhanced aperture plate-detection functionalities and/or capabilities, and/or enhanced sample placement functionalities and/or capabilities.

These and other advantageous features, functionalities and capabilities are provided according to the advantageous colorimetric/spectrophotometric systems and subassemblies/components thereof that are disclosed herein.

SUMMARY OF THE DISCLOSURE

The disclosed colorimetric/spectrophotometric systems and subassemblies/components thereof of the present disclosure have wide-ranging applications in the field of color measurement. In an exemplary application, however, the disclosed systems and subassemblies/components thereof may be advantageously incorporated (in whole or in part) into a sphere-based spectrophotometer, such as the Color i™ 5 spectrophotometer that is commercially available from the assignee of the present application (GretagMacbeth LLC, New Windsor, N.Y.). Reference is also made to commonly assigned U.S. Pat. No. 6,424,413 to Weber et al., which relates to optical measurement systems utilizing integrating sphere technology, the entire contents of which being hereby incorporated by reference.

The Color-i™ 5 spectrophotometer is a sphere-based laboratory spectrophotometer that offers advantageous flexibility, e.g., data compatibility with 10 nm or 20 nm historical data, exceptional measurement versatility of non-uniform samples and a choice of mechanical or video previewing. The Color i™ 5 includes a built-in profile that allows users to select between measurement compatibility with legacy data or more current, higher precision data. The Color i™ 5 spectrophotometer may be employed with the NetProfiler™ system available from GretagMacbeth LLC, which is a web-based application that allows entire networks of spectrophotometers to be remotely monitored, calibrated, adjusted and certified—all via the Internet.

According to an exemplary embodiment of the present disclosure, a spectrophotometric system is provided that includes an integrating sphere. The integrating sphere includes a sample port, an SCE measurement port and an SCI measurement port. In preferred embodiments of the present disclosure, the integrating sphere further includes a reference beam port. A first plurality of mirrors are provided that are positioned relative to the integrating sphere for reflecting and directing an SCE beam emitted from the integrating sphere toward an SCE fiber block. A second plurality of mirrors are provided that are positioned relative to the integrating sphere for reflecting and directing an SCI beam emitted from the integrating sphere toward an SCI fiber block. In addition, first and second focusing lenses are positioned intermediate the first and second plurality of mirrors, respectively, for focusing the SCI and SCE beams.

The first and second focusing lenses are advantageously mounted to a lens carrier that is movably mounted relative to the integrating sphere. By mounting the first and second focusing lenses to a single, axially translatable lens carrier, the disclosed zoom lens assembly ensures that the focusing lenses create an equal path length for the SCE and SCI beams. Moreover, simultaneous movement of the focusing lenses ensures that the SCE and SCI beams measure the same area of a sample of interest. A drive mechanism is coupled to the lens carrier and is operative to reposition the lens carrier relative to the integrating sphere. In a preferred embodiment of the present disclosure, the drive mechanism takes the form of a positioning stepper motor that is coupled to the lens carrier by way of a drive shaft. A positioning slide may also be provided to interact with the lens carrier to facilitate translation of the lens carrier relative to the integrating sphere.

The disclosed spectrophotometric system is advantageously configured to capture a reference beam emitted from a reference beam port defined in the integrating sphere, as well as the SCE and SCI beams, so as to simultaneously process all three beams with a processor associated with the spectrophotometric system. The lens carrier and the first and second focusing lenses define a zoom lens assembly that is configured to create an equal path length for the SCE and SCI beams. Of note, the zoom lens assembly is effective for measuring multiple areas of interest on a sample as to both transmission and reflectance.

According to further disclosed spectrophotometric systems, an aperture plate detection assembly is provided. An exemplary aperture plate detection assembly according to the present disclosure includes an aperture plate holder, a detection disk and an aperture plate. The detection disk advantageously includes a plurality of sensors deployed in a predetermined manner, and the aperture plate generally includes an activation ring that engages a preset fraction of the sensors, thereby identifying the aperture plate. The aperture plate holder typically includes a plurality of magnets for magnetic engagement with the aperture plate.

According to a further embodiment of the disclosed spectrophotometric system, a sample holder assembly is provided that includes a sample holder and a gas spring for dampening movement of the sample holder relative to the integrating sphere.

In a further disclosed embodiment, an aperture plate detection assembly for use with a spectrophotometric system is provided in which the aperture plate detection system includes (i) an aperture plate holder defining a cavity region and a plurality of magnets directed toward the cavity region, (ii) a detection mechanism mounted with respect to the aperture plate holder, wherein the detection mechanism including a sensor system for use in identifying an aperture plate mounted with respect thereto, and (iii) an aperture plate dimensioned and configured for mounting with respect to the cavity region of the aperture plate holder, wherein the aperture plate includes a structural member for interacting with the sensor system to identify the aperture plate. The sensor system may include a plurality of sensors deployed in a predetermined pattern for identifying aperture plates mounted with respect to the aperture plate holder, or an elastomeric connector that is positioned for interacting with an annular groove formed on an underside of the aperture plate.

In addition, a zoom lens assembly for use with a spectrophotometric system is disclosed wherein the zoom lens assembly includes a lens carrier that is movably mounted with respect to a base, wherein the lens carrier includes first and second focusing lenses fixedly mounted with respect thereto, and a drive mechanism that is coupled to the lens carrier for effecting axial translation of the lens carrier relative to the base.

Additional structural features and operational functionalities associated with advantageous color measurement systems and subassemblies/components thereof according to the present disclosure will be apparent from the detailed description and schematic illustrations which follow, particularly when read and reviewed by a person of skill in the relevant art.

BRIEF DESCRIPTION OF THE DRAWINGS

Structural and functional aspects, features, and advantages of the present disclosure will be understood and the manner of making and using such structures will become more readily apparent when the following description is reviewed by persons skilled in the art in conjunction with the accompanying drawings, wherein.

DETAILED DESCRIPTION OF EXEMPLARY EMBODIMENTS

Figure 1:
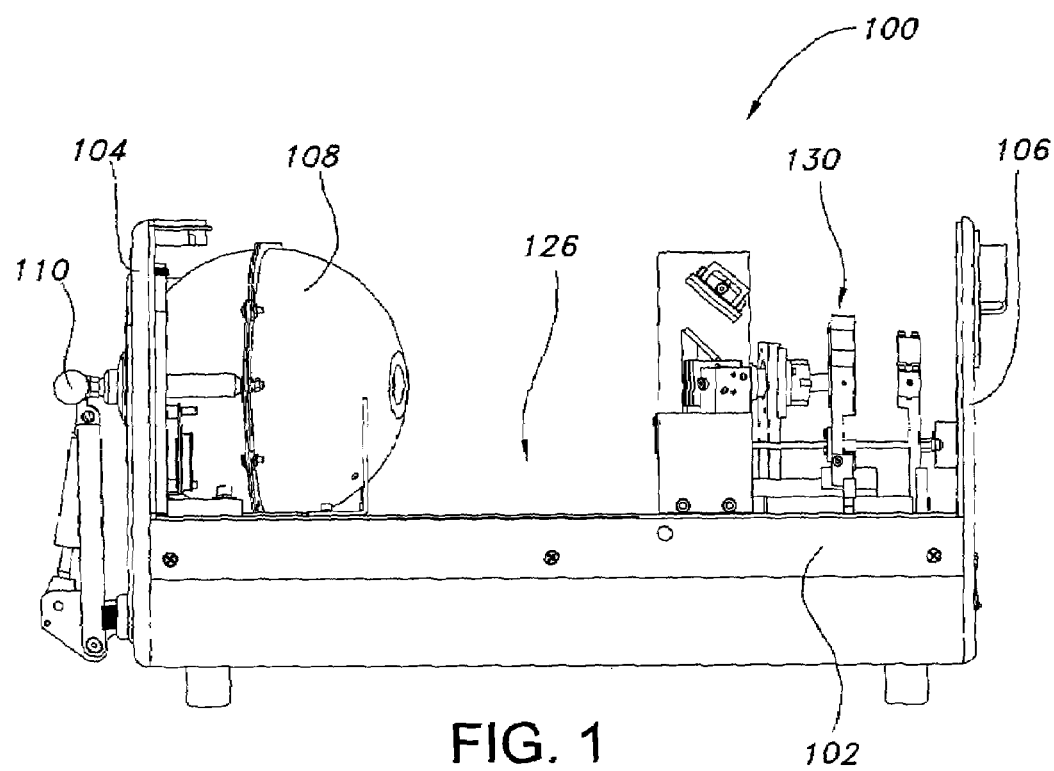
FIG. 1 is a schematic side view of an exemplary spectrophotometric system (with cover removed) according to the present disclosure.

As noted above, the present disclosure provides spectrophotometer systems and subassemblies/components thereof that facilitate: (i) simultaneous measurement of "specular included" and "specular excluded" reflectance properties of a sample through an innovative zoom lens assembly; (ii) transmission measurements of virtually unlimited areas of interest through an innovative zoom lens assembly; (iii) automated and reliable determinations of the type of aperture plate placed at the front of the spectrophotometric instrument through an innovative aperture plate detection assembly; and (iv) reliable and non-disruptive sample placement through an innovative sample holder assembly. Exemplary spectrophotometric systems and subassemblies thereof incorporating the foregoing advantageous structural features and operational functionalities are described below.

The disclosed spectrophotometric systems have wide ranging color measurement utility. Thus, for example, the disclosed spectrophotometric systems may be advantageously employed to make color measurements with respect to fabric, plastic and/or paint samples. In use, the sample is positioned adjacent a sample port of an integrating sphere that forms part of the spectrophotometric system. The sample is illuminated by a light source directed into the integrating sphere, e.g., a xenon flash source, and color information is captured through light gathering optics. A color spectrum analysis is typically effected and color values are calculated, e.g., by an appropriately programmed microprocessor.

The advantageous subassemblies disclosed herein, i.e., the zoom lens subassembly, the aperture plate detection subassembly, and the sample holder subassembly, may be used (either individually or in full or partial combination) in conjunction with a conventional spectrophotometer system, e.g., the above-noted Color i™ 5 spectrophotometer commercially available from GretagMacbeth, LLC. The Color i™ 5 spectrophotometer includes a multi-channel integrating sphere and is generally manufactured to the following product specifications. The product specifications associated with the Color i™ 5 spectrophotometer are representative of exemplary systems that may advantageously employ and/or implement one or more of the subassemblies disclosed herein.

| COLOR I™ 5 SPECTROPHOTOMETER PRODUCT SPECIFICATIONS | |
|---|---|
| Repeatability (White): | 0.03 RMS DE CIELAB |
| Illumination: | Pulsed Xenon, D65 calibrated |
| Spectral Range: | 360 to 750 nm |
| Wavelength Interval: | 10 nm |
| Photometric Range: | 0.0% to 200% reflectance |
| Photometric Resolution: | 0.01% reflectance |
| Apertures – Reflectance: | Large Area View (LAV) 25 mm circular |
| | Medium Area View (MAV) 10 mm circular |
| | Small Area View (SAV) 06 mm circular |
| Transmittance: | Large Area View (LAV) 22 mm circular |
| | Medium Area View (MAV) 10 mm circular |
| | Small Area View (SAV) 06 mm circular |
| Direct Transmittance: | Large Area View (LAV) 22 mm circular |
| Measurement Cycle Time: | <2.5 second max. reflection or transmission |
| Optical Configuration: | Tri-Beam Diffuse/8°, 6 inch Sphere |
| | 2-D CCD array/Holographic grating, simultaneous SCE/SCI, automated UV control, automated lens position |
| Dimensions: | 23 cm W × 25 cm H × 46 cm D |
| Weight: | 12 kgs |
| Temperature: | 10° C. to 35° C. |
| Relative Humidity: | 20 to 80%, non-condensing |
| Electrical Requirements; | 100–240 VAC/50–60 Hz |
| Interface: | USB/RS-232/2400–38400 |

Figure 2:
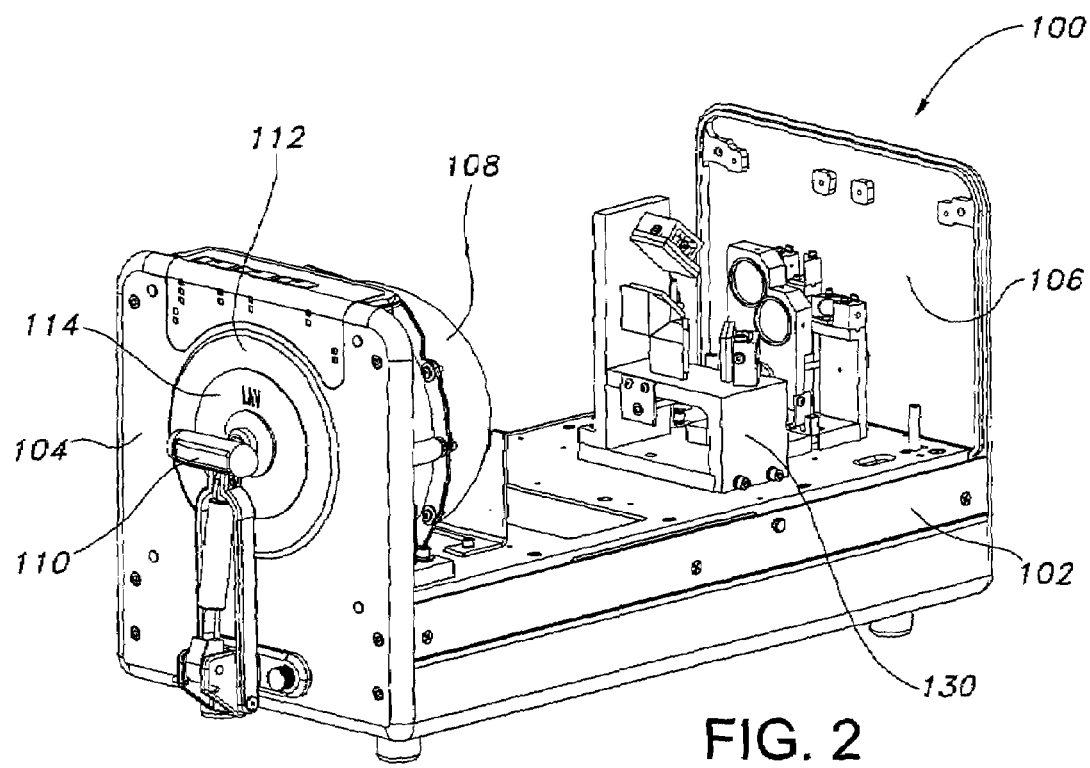
FIG. 2 is a schematic perspective side view of the exemplary spectrophotometric system (with cover removed) of FIG. 1.
Figure 3:
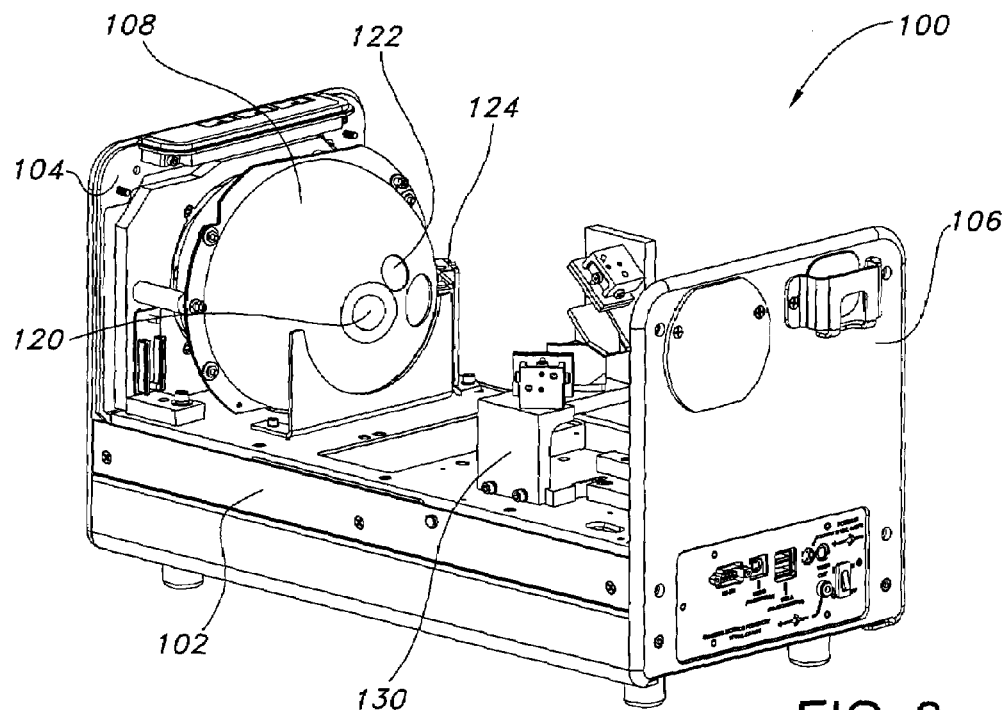
FIG. 3 is a further schematic perspective side view of the exemplary spectrophotometric system (with cover removed) of FIGS. 1 and 2.

With reference to FIGS. 1-3, an exemplary spectrophotometric system 100 that incorporates advantageous subassemblies according to the present disclosure is depicted. System 100 includes a base 102, a front face 104 and a rear face 106. A cover (not pictured) is generally associated with system 100 to enclose the operative components discussed below. The cover has been removed in FIGS. 1-3 to facilitate viewing of such internal componentry. The overall geometry of spectrophotometric system 100 is substantially rectangular, although alternative geometries may be employed as desired, as will be apparent to persons skilled in the art.

With further reference to FIGS. 1-3, an integrating sphere 108 is positioned adjacent front face 104 and is mounted with respect to base 102. Integrating sphere 108 defines a hollow metal sphere, generally several inches or more in diameter, and is coated with a highly reflecting diffuse material. Suitable coating materials include barium sulfate and polytetrafluoroethylene, although alternative materials may be employed provided the desired highly reflective, optically diffuse white interior surface is defined. Integrating sphere 108 includes a sample port (not visible) that opens toward front face 104 and aligns with an aperture defined in front face 104. An advantageous sample holder subassembly 110 may be advantageously mounted with respect to front face 104, as described in greater detail below. Sample holder subassembly 110 operates to reliably position a sample (e.g., a fabric/textile, plastic or paint sample) in alignment with the sample port defined in integrating sphere 108.

Integrating sphere 108 is configured to collect all the light reflected from the surface of a sample placed against the noted sample port which opens into the sphere. One user-controlled parameter generally associated with color measurements taken with the disclosed spectrophotometric system 100 involves the sample's "area of view," i.e., the size of the sample region subject to illumination and color measurement. The "area of view" is advantageously selected/controlled through use of an aperture plate having a desired aperture size. Thus, for example, a set of aperture plates may be provided for use with system 100, such set including a first aperture plate that includes a circular apertures of 25 mm diameter (i.e., large area view or "LAV"), a second aperture plate that includes a circular aperture of 10 mm diameter (i.e., medium area view or "MAV"), and a third aperture plate that includes a circular aperture of 6 mm diameter (i.e., small area view or "SAV"). Alternative aperture plate dimensions may be employed in addition to, or instead of, the foregoing three-plate set, as will be apparent to persons skilled in the art.

With reference to FIG. 2, an aperture plate subassembly 112 that includes an aperture plate detection system is schematically depicted. Aperture plate subassembly 112 includes an aperture plate 114 positioned against front face 104 of spectrophotometric system 100. The central aperture formed in aperture plate 114 aligns with the sample port of integrating sphere 108, thereby facilitating color measurements with respect to a sample positioned in alignment with such central aperture. The design and operation of aperture plate subassembly 112 is described in greater detail below.

With further reference to integrating sphere 108, the illumination effected by the illumination source, e.g., pulsed xenon that is calibrated to provide D65 illumination (i.e., CIE daylight with a correlated color temperature of 6500 K), is essentially independent of the direction and location of the incident beam as well as the size of the beam. As shown in FIG. 3, exemplary integrating sphere 108 includes two distinct measurement ports, namely SCE (specular component excluded) measurement port 120 and SCI (specular component included) measurement port 122. Thus, spectrophotometric system 100 is configured for measuring spectral reflectance properties of a sample placed in front of the illumination/integrating sphere 108 thereof.

In addition, a reference beam fiber housing 124 advantageously cooperates with integrating sphere 108, thereby permitting a reference beam to be captured and transmitted to the processor associated with system 100 for calibration purposes. Thus, the disclosed system 100 is configured for "tri-beam" measurement functionality, by simultaneously taking measurements from the SCI and SCE optical paths (using measurement ports 120 and 122, respectively) and a reference measurement from a third optical path that optically communicates with the optical fiber positioned within fiber housing 124. The SCI and SCE optical paths travel from measurement ports 120 and 122, respectively, and across a transmission region 126 (see FIG. 1) within system 100 to light gathering optics which are discussed in greater detail below.

Light gathering optics according to exemplary embodiments of the present disclosure include a zoom lens assembly 130. Zoom lens assembly 130 is mounted with respect to base 102 of system 100 such that operative elements thereof are movable/translatable with respect to base 102. Zoom lens assembly 130 includes a dual zoom functionality that enhances the effectiveness and utility of exemplary spectrophotometer system 100. Although the disclosed zoom lens assembly 130 may be advantageously employed in conjunction with the schematically depicted spectrophotometric system 100 of FIGS. 1-3, and may be advantageously incorporated into commercially spectrophotometric systems, such as the GretagMacbeth's Color i™ 5 spectrophotometer, the disclosed zoom lens assembly 130 may also be advantageously incorporated into alternative color measurement instrumentation, as will be readily apparent to persons skilled in the art.

Figure 4:
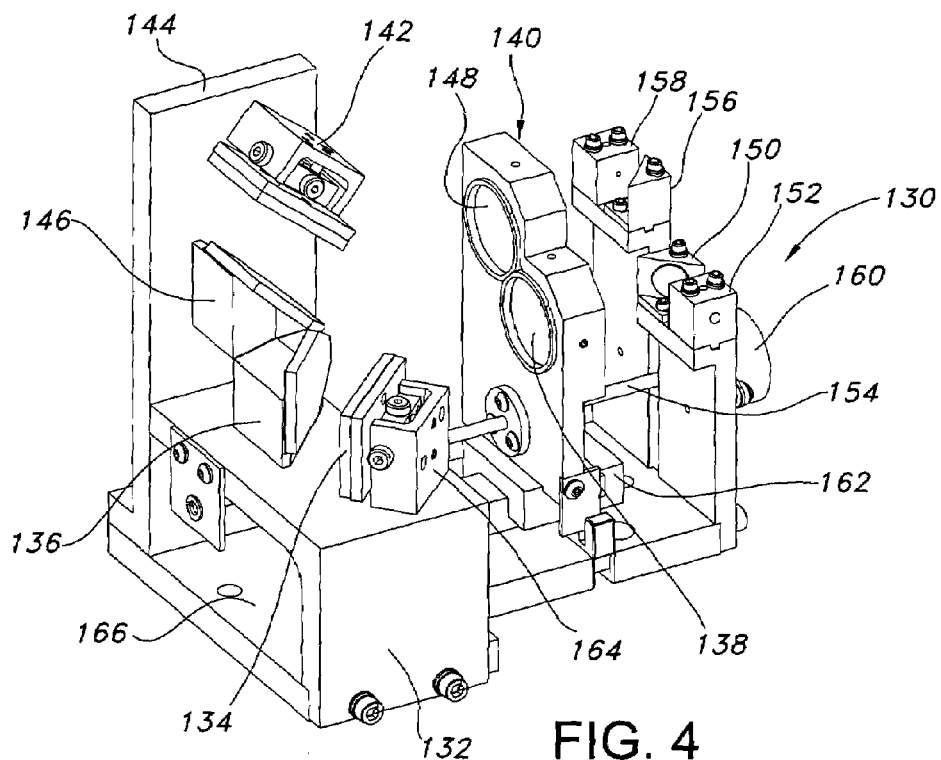
FIG. 4 is a schematic perspective side view of an exemplary zoom lens subassembly for use in conjunction with a spectrophotometric system according to the present disclosure.
Figure 5:
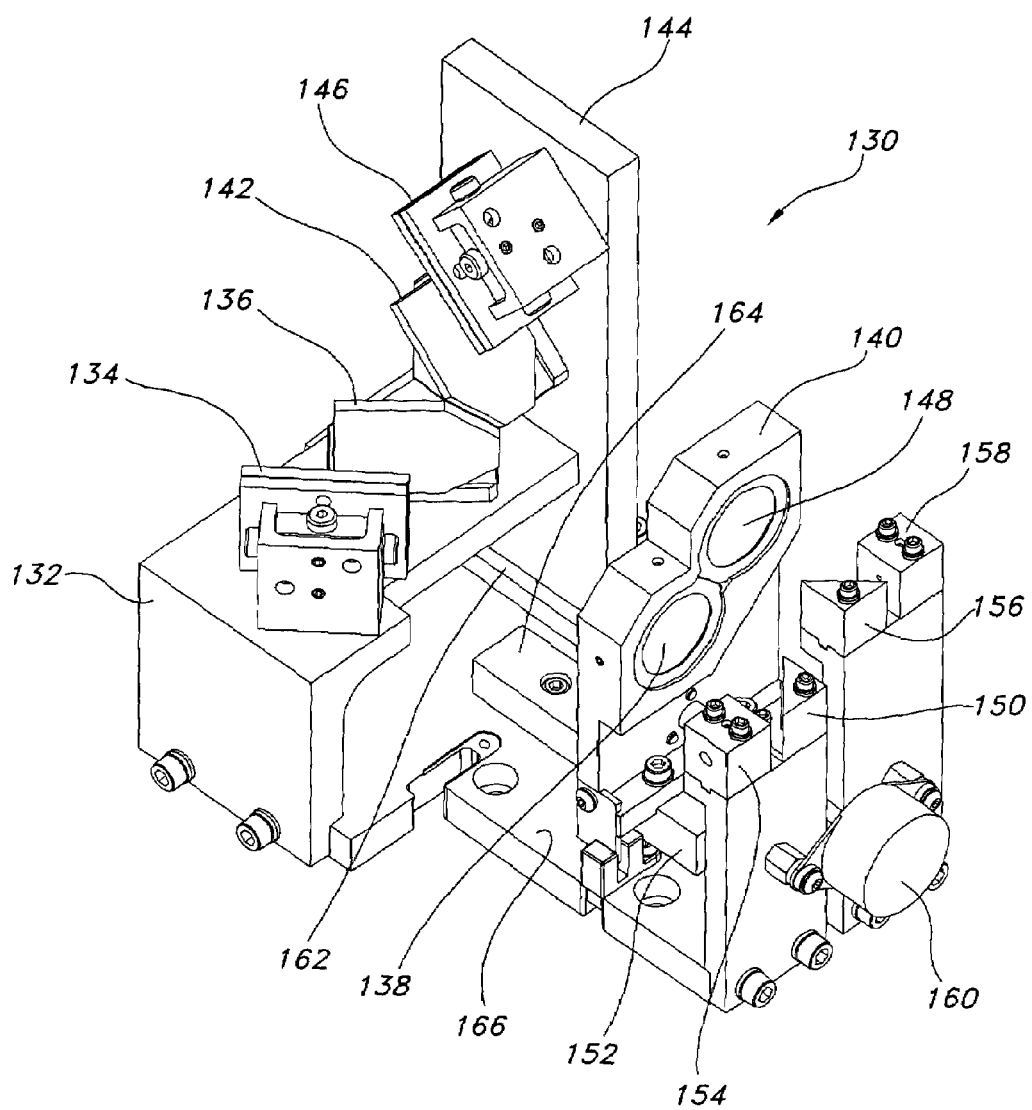
FIG. 5 is a further schematic perspective view of the exemplary zoom lens subassembly of FIG. 4 according to the present disclosure.
Figure 6:
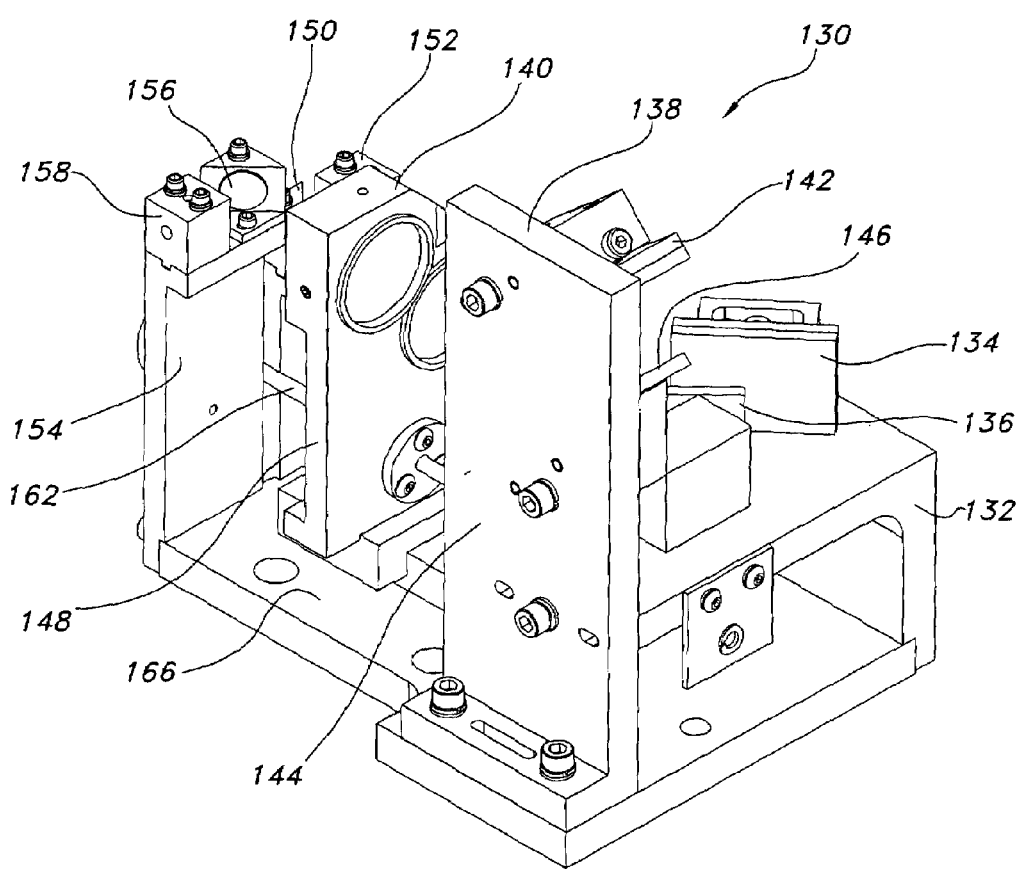
FIG. 6 is an additional schematic perspective view of the exemplary zoom lens subassembly schematically depicted FIGS. 4 and 5.

Zoom lens assembly 130 generally includes a plurality of mirrors and a pair of focusing lenses that are mounted with respect to a translatable lens carrier. The mirrors and lenses define "light gathering optics" for facilitating color measurements according to the present disclosure. A motor or other mechanical drive means is provided for effecting movement/translation of the lens carrier with respect to the mirrors, thereby facilitating zoom functionalities associated therewith. Thus, with additional reference to FIGS. 4-6, zoom lens assembly 130 includes a first elevated support base 132 upon which are mounted a cooperating pair of mirrors for capturing the SCE light beam that is emitted from SCE port 120.

With initial reference to the SCE beam, such beam travels across transmission region 126 in the horizontal plane and impinges upon SCE adjustable fold mirror 134. The SCE beam is reflected so as to impinge upon SCE fold mirror 136 which redirects the SCE beam toward SCE focusing lens 138 which is mounted in lens carrier 140. As such, the SCE beam is a horizontally aligned beam. The SCE focusing lens 138 focuses the SCE beam on an SCE fiber fold mirror 150 which redirects the beam to an SCE fiber block 152. Both the SCE fiber fold mirror 150 and SCE fiber block 152 are mounted on a rear support wall 154 and are generally in the same horizontal plane. The SCE fiber optic (not pictured) is positioned within the SCE fiber block 152, such that the SCE beam is captured thereby and transmitted to a processor, e.g., a multi-channel analyzer.

In like measure, an SCI beam is emitted from SCI port 122, travels across transmission region 126 in the horizontal plane and impinges upon SCI adjustable fold mirror 142 which is mounted relative to side support wall 144. SCI adjustable fold mirror 142 redirects the SCI beam toward SCI fold mirror 146, which redirects the SCI beam toward SCI focusing lens 148, which is also mounted within lens carrier 140. The SCI beam is thus a vertically aligned beam. The SCI focusing lens 148 focuses the SCI beam on an SCI fiber fold mirror 156 which redirects the beam to an SCI fiber block 158. Both the SCI fiber fold mirror 156 and SCI fiber block 158 are mounted on rear support wall 154, but in a different horizontal plane relative to the corresponding SCE structural elements. The SCI fiber optic (not pictured) is positioned within the SCI fiber block 158, such that the SCI beam is captured thereby and transmitted to a processor, e.g., the same multi-channel analyzer that receives the SCE transmission.

Thus, in use, the optical path starts from the illumination/integrating sphere 108 for all three beams (SCI, SCE and reference beams). The SCE beam travels from the sphere in the horizontal plane to the SCE adjustable fold mirror to the SCE Fold Mirror, through the SCE Focusing Lens, to the SCE Fiber Fold Mirror, to the SCE Fiber Block, which contains the SCE Fiber Optic, which transmits the light to a multi-channel analyzer. The SCI beam follows a comparable, parallel path to the multi-channel analyzer. In addition, the reference beam is focused by a separate focusing lens (not shown) and is captured by a fiber optic (not shown) for transmission to the multi-channel analyzer (not shown). The design and implementation of such focusing/transmission structures is well within the skill of persons skilled in the art based on the disclosure herein.

The disclosed light gathering optical system and the reference beam optical system are designed to simultaneously take measurements from the SCI and SCE optical paths, and to take a "reference" measurement of the illumination source from a third optical path. This advantageous design constitutes a "tri-beam" measurement apparatus which represents a marked improvement over the industry standard "dual-beam" measurement that consists of either the SCI and reference measurement or the SCE and reference measurement. Of note, currently available commercial systems provide a method of switching between SCI and SCE by mechanical means, but do not offer the ability to obtain simultaneous measurements, as disclosed herein.

Another particularly advantageous feature associated with the exemplary zoom lens assembly 130 disclosed herein relates to lens carrier 140 which houses both the SCE and SCI focusing lenses 138, 148, respectively, thus establishing an equal path length for both the SCE and SCI beams. This structural arrangement insures that both beams measure the same area of interest on the sample. Both lenses move along the instrument axis simultaneously based on drive forces imparted by way of a motor 160, e.g., a positioning stepper motor or other drive mechanism. Motor 160 is mounted to rear support wall 154 and drive shaft 162 extends therethrough so as to engage lens carrier 140. Drive shaft 162 also serves to guide axial movement of lens carrier 140.

Lens carrier 140 is movably mounted relative to a slide track 164 that is aligned with the axis of the color measurement instrument. Although the exemplary slide track 164 shown in FIGS. 4-6 extends above floor 166 and features a substantially rectangular cross-section, alternative configurations may be implemented, e.g., trapezoidal cross-sections, one or more elongated channels formed in floor 166, or the like. Stop surfaces may be incorporated into side track 164 to limit movement of lens carrier 140 within a prescribed travel distance, as will be apparent to persons skilled in the art. Electronic sensors may be associated with such stop surfaces and may communicate with motor 160 to cut-off translational movement of lens carrier 140 at predetermined locations. Movement of lens carrier 140 relative to an associated illumination/integrating sphere is generally software controlled. Thus, an operator is generally permitted to select a desired area of interest on the sample to be measured, and the software translates such area of interest to an appropriate lens carrier position relative to the illumination/integrating sphere. Motor 60 is then activated, as needed, to axially reposition lens carrier 140 to a desired location. Sensor mechanism(s) are generally provided on lens carrier 140 and/or complementary structures (e.g., slide track 164) to sense/signal when lens carrier 140 has reached the desired axial location. The design and implementation of axial repositioning software for use in cooperation with a motor or other drive mechanism, as described herein, is well within the skill of persons of ordinary skill in the present field.

The nature of the disclosed lens carrier design allows for almost unlimited areas of interest to be measured by both SCE and SCI beams. The foregoing advantageous functionality associated with the disclosed zoom lens assembly 130 also yields beneficial results when the spectrophotometer is operated to obtain spectral measurements in a "transmission mode." Only the SCE beam is used for transmission measurements, but the zoom lens assembly 130 advantageously allows for almost unlimited areas of interest to be measured on the sample while in the transmission mode.

Spectral data obtained using the "tri-beam" architecture of the present disclosure typically takes the form of three data streams, simultaneously collected, which may be directed through conventional transmission systems to a conventional processor. The zoom lens assembly of the present disclosure, wherein first and second lenses are translated together along the instrument axis, facilitates reliable, efficient and flexible spectral measurements, both in the reflective and transmissive modes. Further structural features and operational benefits associated with the disclosed zoom lens assembly of the present disclosure will be readily apparent to persons skilled in the art from this description and the accompanying figures.

Turning to FIGS. 2 and 7-9, an advantageous aperture plate assembly 112 with aperture plate detection functionality is disclosed. The disclosed aperture plate assembly 112 may be advantageously incorporated into and/or used in conjunction with a spectrophotometric system, e.g., the GretagMacbeth Color i™ 5 spectrophotometer system. The disclosed aperture plate assembly 112 allows the instrument to automatically and reliably determine which type of aperture plate has been placed on the front of the spectrophotometric instrument, regardless of the circumferential orientation of the aperture plate.

The disclosed aperture plate assembly 112 incorporates a novel plate design that obviates the orientation issue associated with commercially available detection systems. Exemplary aperture plate assembly 112 includes an annular ring design as part of the plate construction, thus providing an orientation-free detection method. The disclosed aperture plate assembly typically includes one or more magnets, e.g., a set of magnets, which act to hold the aperture plate in place relative to the spectrophotometric system/instrument. According to exemplary embodiments of the disclosed aperture plate assembly, aperture plate detection functionality is associated with an aperture plate holder by way of suitable attachment means, e.g., a pressure sensitive adhesive layer on an aperture plate detector. While the exemplary attachment mechanisms disclosed herein, e.g., magnet(s) and adhesive layers, are effective in achieving the desired interplay between individual components, alternative attachment mechanisms may be employed without departing from the present disclosure, as will be apparent to persons skilled in the art.

Figure 7:
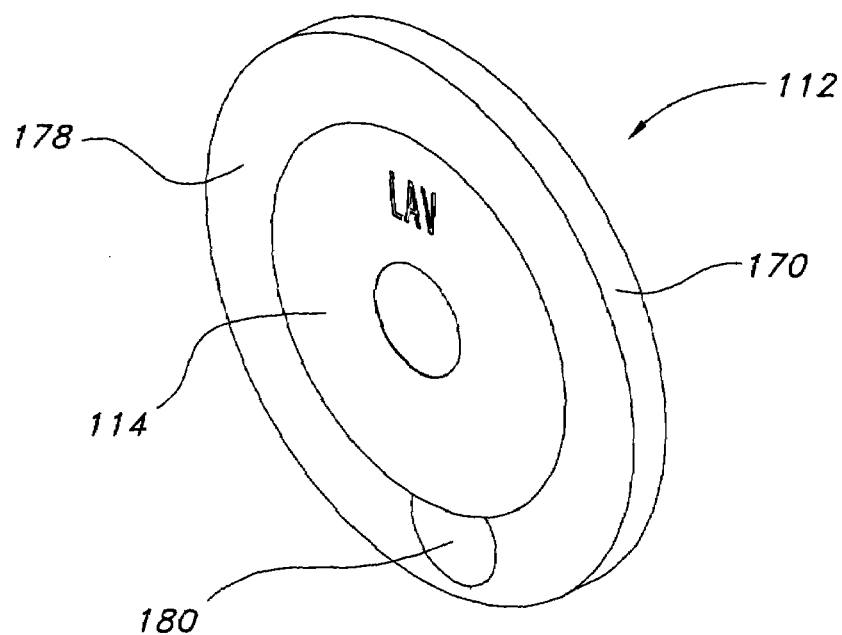
FIG. 7 is a schematic perspective view of an exemplary aperture plate subassembly that includes an aperture plate detection system for use in conjunction with a spectrophotometric system according to the present disclosure.
Figure 8:
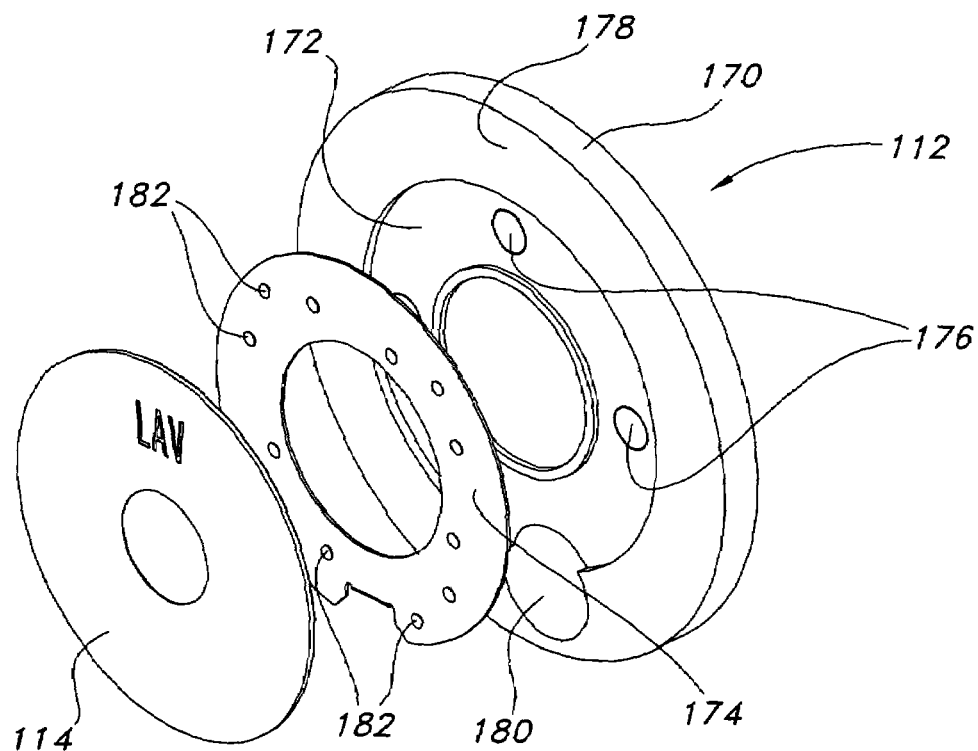
FIG. 8 is an exploded perspective view of the exemplary aperture plate subassembly of FIG. 7.
Figure 9:
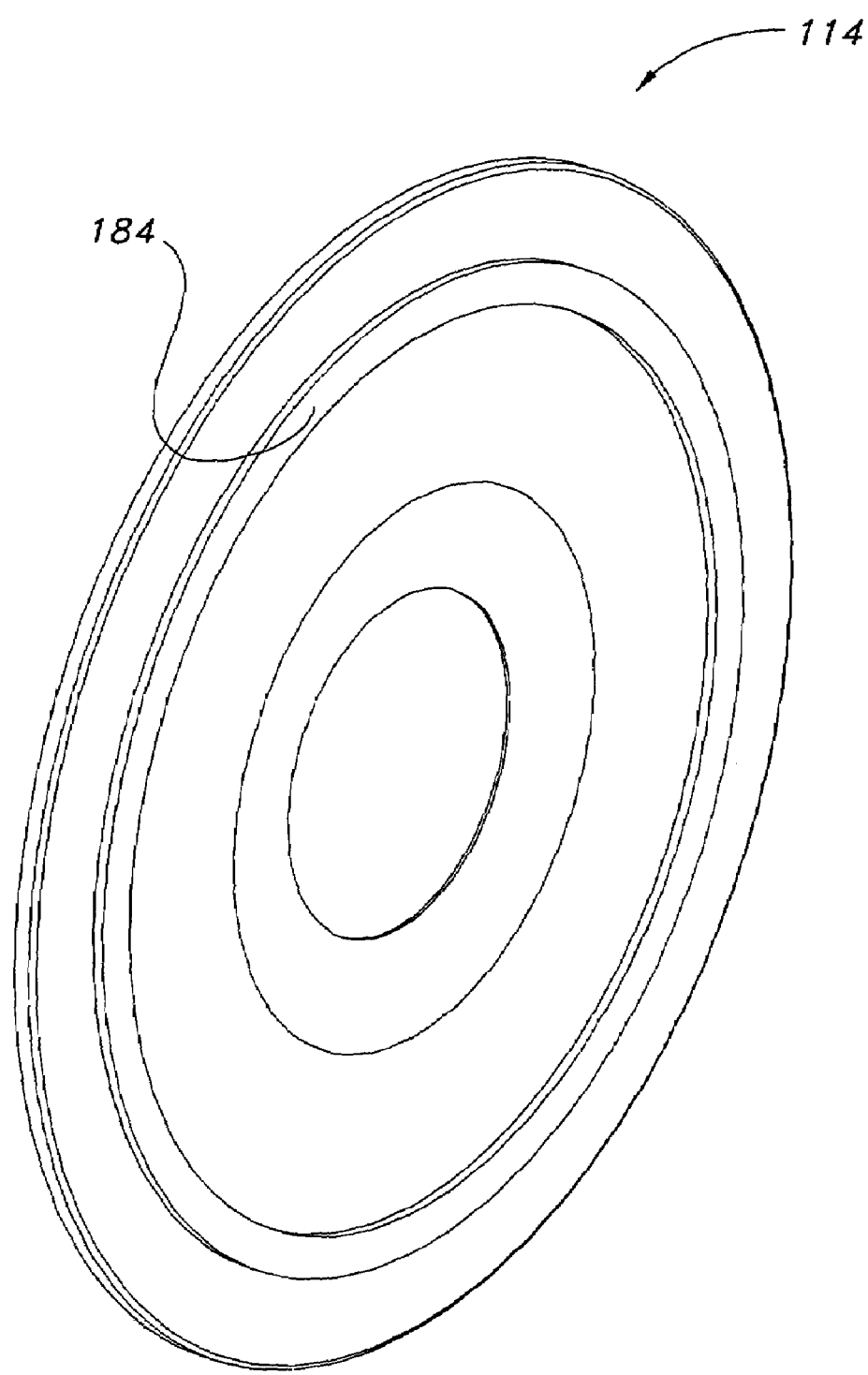
FIG. 9 is a schematic perspective view of a rear side of an exemplary aperture plate member according to the present disclosure.

With particular reference to FIGS. 7-9, exemplary aperture plate assembly 112 includes an aperture plate holder 170 which is configured and dimensioned for receipt of an aperture plate 114. Aperture plate holder 170 is generally circular in outer dimension, and defines a circular cavity region 172 for receipt of aperture plate 114, as well as detection disk 174. Thus, aperture plate holder 170 includes one or more structural features that provide lateral retention to keep aperture plate concentric to detection disk 174, e.g., a circumferential cavity sized and dimensioned to receive aperture plate 114 and detection disk 174 therewithin. Detection disk 174 is typically adhered to aperture plate holder 170, e.g., through an appropriate adhesive or the like. A plurality of spaced magnets 176 are positioned in aperture plate holder 170 and oriented toward cavity region 174. The depth of cavity region 174 is generally selected so as to accommodate detection disk 174 and aperture plate 114 therewithin. Thus, as shown in FIG. 7, a substantially planar surface is defined by the annular region 178 of annular plate holder 170 and aperture plate 114, once aperture plate assembly 112 is fully assembled. One or more scallops 180 are formed in annular region 178 to facilitate detachment of aperture plate 114 and/or detection disk 174 therefrom.

The advantageous detection system associated with the disclosed aperture plate assembly 114 utilizes a plurality of detector switches/sensors 182 deployed with respect to detection disk 174. In the disclosed exemplary embodiment, a raised annular activation ring 184 (see FIG. 9) is formed on the underside of aperture plate 114. Activation ring 184 presses on the correspondingly aligned detector switches/sensors 182 that are deployed on detection disk 174. The pattern of the detector switches/sensors 182 on detection disk 174 is configured to reliably identify the aperture plate brought into contact therewith. Thus, for example, the radial spacing of the detector switches/sensors 182 is defined so that annular activation ring 184 of a first aperture plate contacts a first predetermined set of detector switches/sensors 182, whereas the annular activation ring 184 of a second aperture plate contacts a second predetermined set of detector switches/sensors 182. In short, the annular ring radii of the annular activation rings associated with different aperture plates is utilized, in conjunction with the radially spaced activation switches/sensors 182 and processing capabilities associated with such activation switches/sensors, to reliably identify the aperture plate(s) brought into contact therewith.

Circumferential detector switch redundancy is advantageously incorporated into the activation switch deployment geometry, to further increase the reliability of the detection functionality associated with the disclosed aperture plate assembly 112. In an exemplary embodiment of the disclosed aperture plate assembly associated with the GretagMacbeth Color i™ 5 spectrophotometer, activation switches/sensors are deployed so as to define multiple ring geometries providing fifteen (15) possible unique aperture plates. Alternative activation switch deployment patterns may be employed according to the present disclosure, as will be apparent to persons skilled in the art.

An alternate aperture plate detection system and methodology are disclosed herein. In this alternative exemplary embodiment, the same annular ring/plate concept is employed with the exception that the raised annular ring is replaced with an annular groove. To reliably identify the aperture plate brought into contact with a detection disk associated with the aperture plate assembly, an elastomeric connector is used to electrically detect the groove width. Alternative sensor systems may be employed based on the teachings contained herein, without departing from the spirit or scope of the present disclosure, as will be readily apparent to persons skilled in the art.

In operation, detection disk 174 is adhered or otherwise fixed relative to aperture plate holder 170 (e.g., by way of key/slot arrangement, engagement detents, or the like). A user places a desired aperture plate 114 (e.g., the LAV aperture plate schematically depicted in FIGS. 2, 7 and 8) within cavity region 174 without regard to circumferential orientation. The magnets 176 associated with aperture plate holder 170 retain aperture plate 114 relative to the aperture plate holder. In addition, activation ring 184 on the underside of aperture plate 114 engages a set of detector switches/sensors 182 deployed on detection disk 174. Based on the pattern of detector switches/sensors 182 engaged by activation ring 184, a processor associated with aperture plate assembly and in communication with detector switches/sensors 182 determines which of the pre-programmed aperture plates has been inserted therein. The disclosed aperture plate detection system is reliable, efficient and sufficiently versatile in detector switch/sensor deployment to accommodate and identify a multiplicity of aperture plates.

Figure 10:
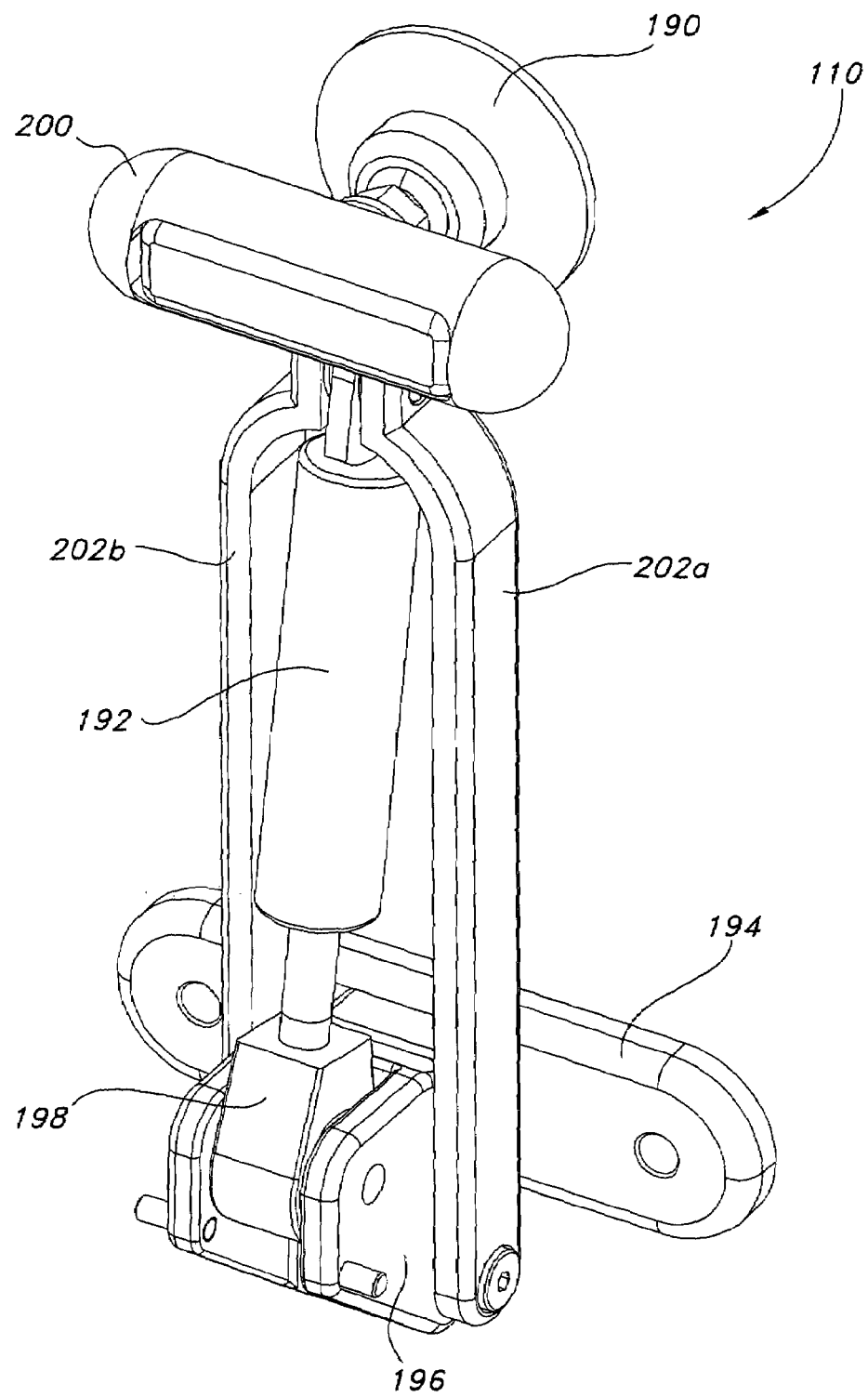
FIG. 10 is a schematic side view of an exemplary sample holder subassembly for use in conjunction with a spectrophotometric system according to the present disclosure.

Turning to FIGS. 2 and 10, an exemplary sample holder assembly 110 is depicted according to the present disclosure. The disclosed sample holder assembly 110 may be advantageously incorporated into and/or used in conjunction with a spectrophotometric system or other color measurement instrument, e.g., the GretagMacbeth Color i™ 5 spectrophotometer system. The disclosed sample holder assembly 110 provides a method for securing a sample under test to the color measurement instrument (e.g., a spectrophotometric system) via pressure placed on the sample by a sample pad 190, without disruption and/or damage to the instrument or the alignment/calibration of the measuring system.

Sample holder assembly 110 advantageously employs a dampened gas spring 192 to moderate movement of sample holder 190 relative to the spectrophotometer. This mechanically reliable single unit design provides a linearly constant spring force which advantageously retains the sample under test in fixed position against the instrument, and also provides an "over-centered" position in which the sample holder 190 will remain open. Once sample holder 190 is moved from the "over-centered" position, the dampening feature of the gas spring 192 prevents the "mouse-trap" or snap action typically associated with prior "over-centered" spring designs. This dampening property associated with gas spring 192 produces a smooth return of sample holder 190 to the illumination sphere, thus eliminating damage to the sphere.

Thus, with particular reference to FIG. 10, sample holder assembly 110 includes a mounting plate 194 for mounting relative to a front face 104 of a spectrophotometric system 100. A bracket 196 extends from mounting plate 194 and typically defines a yoke for pivotal interaction with mounting arm 198 of gas spring 192. Outer bracket arms 202*a*, 202*b* are pivotally mounted with respect to the outerward faces of bracket 196. A handle 200 is positioned at the upper end of bracket arms 202*a*, 202*b*. The upper ends of bracket arms 202*a*, 202*b* define a constricted region that engages gas spring 192, such that gas spring 192 imparts a force thereagainst.

Handle 200 permits a user to pivot sample holder 190 away from a spectrophotometric instrument (see FIG. 1). As the sample holder 190 is moved away from the spectrophotometric instrument, a force is imparted against gas spring 192 by the constricted region defined by bracket arms 202*a*, 202*b*, thereby loading gas spring 192. Thereafter, when the sample holder 190 is moved toward the spectrophotometric system, the gas spring 192 prevents the snap action typically associated with over-centered spring designs. Rather, the gas spring 192 functions to effect a smooth return of the sample holder 190 into engagement with the color measurement instrument.

Figure 11:
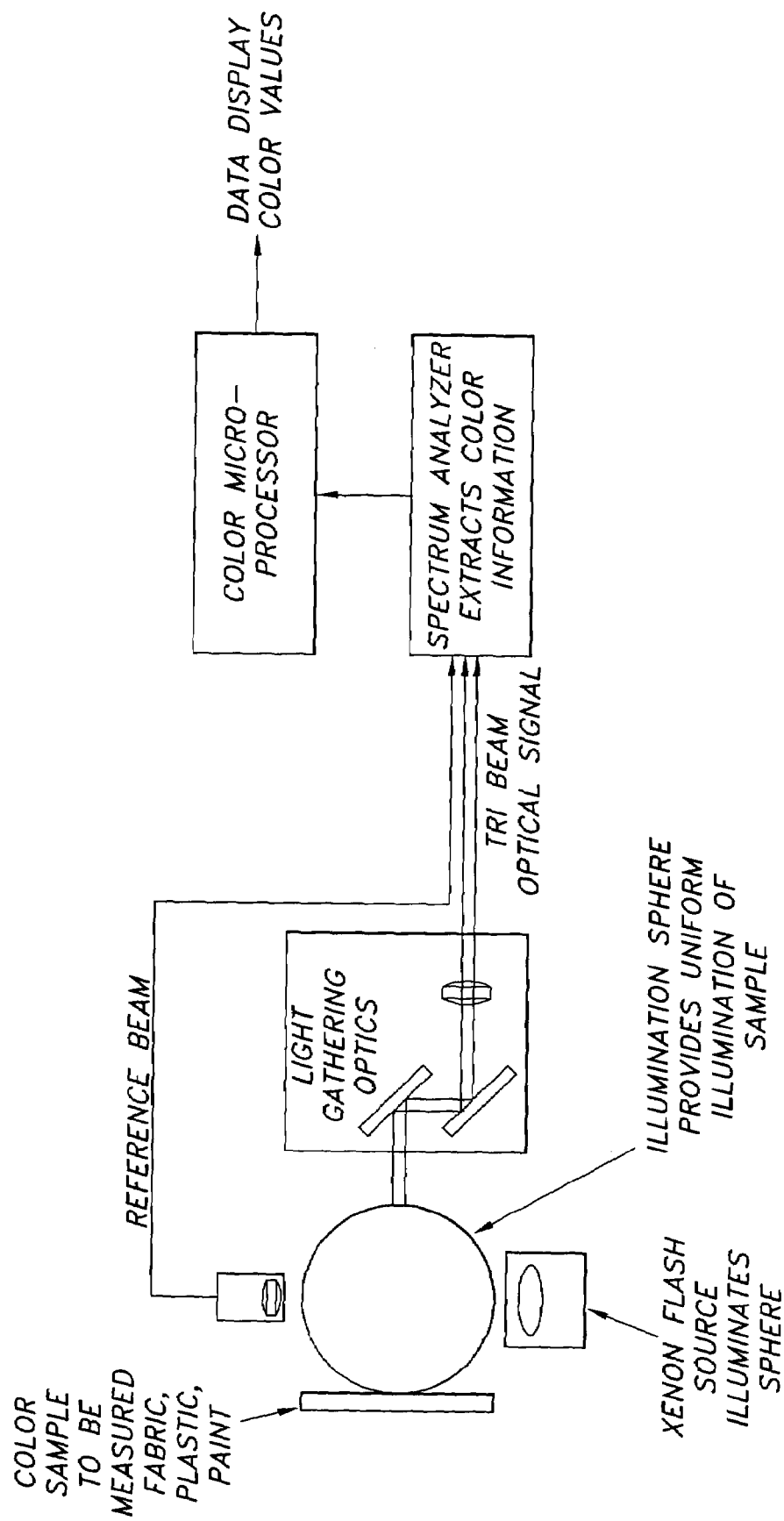
FIG. 11 is a block diagram of a color measurement process utilizing a spectrophotometric system according to the present disclosure.

To further assist persons of skill in the art in making and using enhanced spectrophotometric assemblies (and components/subassemblies thereof) according to the present disclosure, reference is made to FIG. 11 which provides a flow chart of a color measurement methodology according to an implementation of exemplary embodiments of the present disclosure. As shown therein, a tri-beam measurement modality is advantageously effected simultaneously, thereby enhancing available color measurement regimens.

Although the present disclosure has been provided with reference to exemplary embodiments thereof, the present disclosure is not to be limited thereto. Rather, modifications, enhancements and/or variations to the disclosed systems and assemblies are contemplated, and such modifications, enhancements and/or variations will not depart from the spirit or scope of the present disclosure. Moreover, it is specifically contemplated that one or more of the disclosed structures may be employed in a spectrophotometric application, but that it is not necessary that all such structures be implemented to realize the benefits associated with each structure individually. For example, one or more of the disclosed zoom lens assembly, aperture plate assembly with detection functionality and/or sample holder assembly may be implemented, in whole or in part, without departing from the spirit or scope of the present disclosure. Thus, persons of skill in the art will understand that the advantageous structures disclosed herein may be employed, in whole or in part, as may be desired to achieve specific design and/or operational objectives and/or requirements.

The invention claimed is:

1. A spectrophotometric system comprising: (a) an integrating sphere that includes a sample port, an SCE measurement port and an SCI measurement port; (b) a first plurality of mirrors positioned relative to said integrating sphere for reflecting and directing an SCE beam emitted from said integrating sphere toward an SCE fiber block; (c) a second plurality of mirrors positioned relative to said integrating sphere for reflecting and directing an SCI beam emitted from said integrating sphere toward an SCI fiber block; and (d) first and second focusing lenses positioned intermediate said first and second plurality of mirrors, respectively, for focusing said SCI and SCE beams, said first and second focusing lenses being mounted to a lens carrier that is movably mounted relative to said integrating sphere; and (e) a drive mechanism that is coupled to said lens carrier and operative to reposition said lens carrier relative to said integrating sphere.

2. A spectrophotometric system according to claim 1, further comprising a reference beam measurement port defined in said integrating sphere.

3. A spectrophotometric system according to claim 2, wherein a reference beam is emitted from said reference beam port, and wherein said reference beam, said SCE beam and said SCI beam are simultaneously processed by a processor associated with said spectrophotometric system.

4. A spectrophotometric system according to claim 1, wherein said drive mechanism includes a stepper motor.

5. A spectrophotometric system according to claim 1, further comprising a positioning slide which interacts with said lens carrier to facilitate translation of said lens carrier relative to said integrating sphere.

6. A spectrophotometric system according to claim 1, wherein said lens carrier and said first and second focusing lenses defines a zoom lens assembly, and wherein said zoom lens assembly is configured to create an equal path length for the SCE and SCI beams.

7. A spectrophotometric system according to claim 6, wherein said zoom lens assembly is effective for measuring multiple areas of interest on a sample as to both transmission and reflectance.

8. A spectrophotometric system according to claim 1, further comprising an aperture plate detection assembly positioned relative to said sample port for selecting an area of view for a sample.

9. A spectrophotometric system according to claim 8, wherein said aperture plate detection assembly includes an aperture plate holder, a detection disk and an aperture plate.

10. A spectrophotometric system according to claim 9, wherein said detection disk includes a plurality of sensors deployed in a predetermined manner, and wherein said aperture plate includes an activation ring that engages a preset fraction of said plurality of sensors.

11. A spectrophotometric system according to claim 9, wherein said aperture plate holder includes a plurality of magnets for magnetic engagement with said aperture plate.

12. A spectrophotometric system according to claim 1, further comprising a sample holder assembly that includes a sample holder and a gas spring for dampening movement of said sample holder relative to said integrating sphere.

* * * * *